US012579649B2

(12) United States Patent (10) Patent No.: US 12,579,649 B2

Morita (45) Date of Patent: Mar. 17, 2026

(54) RADIATION IMAGE PROCESSING APPARATUS AND OPERATION METHOD THEREOF

(71) Applicant: FUJIFILM Corporation, Tokyo (JP)

(72) Inventor: Junya Morita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 347 days.

(21) Appl. No.: 18/191,191

(22) Filed: Mar. 28, 2023

(65) Prior Publication Data

US 2023/0316524 A1 Oct. 5, 2023

(30) Foreign Application Priority Data

Mar. 29, 2022 (JP) ................................. 2022-053440

(51) Int. Cl.
*G06K 9/00* (2022.01)
*A61B 6/00* (2006.01)
(Continued)

(52) U.S. Cl.
CPC ............ *G06T 7/0014* (2013.01); *A61B 6/502* (2013.01); *A61B 6/5217* (2013.01); *G06T 2207/10116* (2013.01); *G06T 2207/30068* (2013.01)

(58) Field of Classification Search
CPC ......... G06T 7/0014; G06T 2207/10116; G06T 2207/30068; G06T 2207/20021; A61B 6/502; A61B 6/5217; A61B 6/04; A61B 6/0414; A61B 5/0091; A61B 5/4312; A61B 5/708; A61B 5/4872
See application file for complete search history.

(56) References Cited

U.S. PATENT DOCUMENTS

| | | | |
|---|---|---|---|
| 10,957,039 B2 * | 3/2021 | Morita ................... | G06V 10/25 |
| 2003/0169915 A1 | 9/2003 | Takeo | |

(Continued)

FOREIGN PATENT DOCUMENTS

| | | |
|---|---|---|
| EP | 2366332 A1 | 9/2011 |
| JP | H04341247 A | 11/1992 |

(Continued)

OTHER PUBLICATIONS

The extended European search report issued by the European Patent Office on Aug. 21, 2023, which corresponds to European Patent Application No. 23165055.7-1126 and is related to U.S. Appl. No. 18/191,191.

(Continued)

*Primary Examiner* — Atiba O Fitzpatrick

(74) *Attorney, Agent, or Firm* — Studebaker Brackett PLLC

(57) ABSTRACT

A processor provided in a radiation image processing apparatus acquires two radiation images obtained by imaging breasts of the same subject, calculates, based on the radiation images, a pixel mammary gland ratio, which is a ratio of a mammary gland for each pixel in each of the radiation images, calculates, based on the pixel mammary gland ratio, a region mammary gland ratio in a predetermined region of each of the radiation images, evaluates extensibility of the mammary gland by comparing two region mammary gland ratios respectively calculated using the two radiation images, and performs control to display an evaluation result of the extensibility.

13 Claims, 10 Drawing Sheets

(51) Int. Cl.
        *A61B 6/50*                (2024.01)
        *G06T 7/00*                (2017.01)

(56)                    References Cited

U.S. PATENT DOCUMENTS

| | | | | |
|---|---|---|---|---|
| 2010/0054557 A1* | 3/2010 | Morita | A61B 6/5217 |
| | | | 382/128 |
| 2010/0246924 A1* | 9/2010 | Morita | A61B 6/502 |
| | | | 382/132 |
| 2011/0229006 A1* | 9/2011 | Morita | G06T 7/136 |
| | | | 382/132 |
| 2012/0014505 A1* | 1/2012 | Morita | G06T 5/00 |
| | | | 378/37 |
| 2017/0221201 A1 | 8/2017 | Chang et al. | |
| 2017/0367671 A1* | 12/2017 | Arai | A61B 6/502 |
| 2018/0279982 A1* | 10/2018 | Fukuda | A61B 5/1072 |
| 2019/0304088 A1* | 10/2019 | Morita | A61B 5/0091 |
| 2019/0388045 A1* | 12/2019 | Ohtani | A61B 6/466 |
| 2019/0388046 A1* | 12/2019 | Morita | A61B 6/502 |
| 2019/0388047 A1* | 12/2019 | Morita | A61B 6/5205 |
| 2022/0270306 A1* | 8/2022 | Morita | A61B 6/502 |
| 2023/0190237 A1* | 6/2023 | Noguchi | A61B 8/085 |
| | | | 600/442 |

FOREIGN PATENT DOCUMENTS

| | | | |
|---|---|---|---|
| JP | 2003-334183 A | 11/2003 |
| JP | 2005-131011 A | 5/2005 |
| JP | 2009-291336 A | 12/2009 |
| JP | 2010-051456 A | 3/2010 |
| JP | 2016-142666 A | 8/2016 |
| JP | 2019-177050 A | 10/2019 |

OTHER PUBLICATIONS

"Notice of Reasons for Refusal" Office Action issued in JP 2022-053440; mailed by the Japanese Patent Office on Nov. 18, 2025.

* cited by examiner

| RADIATION IMAGE PROCESSING APPARATUS | 10 |

11 — MODALITY

12 — DATABASE

IMAGE ACQUISITION UNIT — 30

PIXEL MAMMARY GLAND RATIO CALCULATION UNIT — 40

REGION DETERMINATION UNIT — 50

REGION MAMMARY GLAND RATIO CALCULATION UNIT — 60

EXTENSIBILITY EVALUATION UNIT — 70

13 — DISPLAY

DISPLAY CONTROLLER — 80

REGION MAMMARY GLAND RATIO: LOW

REGION MAMMARY GLAND RATIO: HIGH (CORRECTION REQUIRED)

START

ST101 — ACQUIRE RADIATION IMAGES

ST102 — CALCULATE PIXEL MAMMARY GLAND RATIO

ST103 — DETERMINE PREDETERMINED REGION

ST104 — CALCULATE REGION MAMMARY GLAND RATIO

ST105 — OUTPUT EVALUATION RESULT

ST106 — GENERATE DISPLAY IMAGE

END

RADIATION IMAGE PROCESSING APPARATUS AND OPERATION METHOD THEREOF

CROSS-REFERENCE TO RELATED APPLICATIONS

This application claims priority under 35 U.S.C § 119(a) to Japanese Patent Application No. 2022-53440 filed on 29 Mar. 2022. The above application is hereby expressly incorporated by reference, in its entirety, into the present application.

BACKGROUND OF THE INVENTION

1. Field of the Invention

The present invention relates to a radiation image processing apparatus for evaluating extensibility of mammary glands using radiation images and an operation method thereof.

2. Description of the Related Art

In mammography, it is important to appropriately position breasts of a subject in order to capture a radiation image in which interpretation by a doctor and image processing assisting the interpretation are appropriately performed. One evaluation item for discriminating whether the positioning is appropriate is "extensibility of a mammary gland".

As a method of evaluating the extensibility of a mammary gland, a method of evaluation based on an area ratio of a mammary gland region and an intramammary contrast of one radiation image is known (JP2010-51456A). In addition, a method of calculating matching of the shapes of mammary glands using pattern matching between radiation image data of the same subject and determining whether or not a position of a breast and a degree of compression are appropriate is known (JP2009-291336A).

SUMMARY OF THE INVENTION

The method using the area ratio of the mammary gland region and the intramammary contrast for one radiation image or the method using the matching of the shapes of the mammary glands for two radiation images may be insufficient for evaluating the extensibility of the mammary gland.

An object of the present invention is to provide a radiation image processing apparatus capable of improving the accuracy of evaluation of extensibility of a mammary gland and an operation method thereof.

According to an aspect of the present invention, there is provided a radiation image processing apparatus comprising a processor, in which the processor is configured to: acquire two radiation images obtained by imaging breasts of the same subject; calculate, based on the radiation images, a pixel mammary gland ratio, which is a ratio of a mammary gland for each pixel in each of the radiation images; calculate, based on the pixel mammary gland ratio, a region mammary gland ratio in a predetermined region of each of the radiation images; evaluate extensibility of the mammary gland by comparing two region mammary gland ratios respectively calculated using the two radiation images; and perform control to display an evaluation result of the extensibility.

It is preferable that the processor is configured to set, as the predetermined region, a region having the pixel in which the pixel mammary gland ratio is equal to or greater than a first determination threshold value in the radiation image.

It is preferable that the processor is configured to: calculate a mammary gland amount for each pixel using the pixel mammary gland ratio; and set, as the predetermined region, a region having the pixel in which the mammary gland amount is equal to or greater than a second determination threshold value in the radiation image.

It is preferable that the processor is configured to set, as the predetermined region, a region within a specific distance range from the pixel in which the pixel mammary gland ratio is maximum in the radiation image.

It is preferable that the processor is configured to evaluate the extensibility based on a difference between two region mammary gland ratios respectively calculated using the radiation image.

It is preferable that the region mammary gland ratio is a statistic of the pixel mammary gland ratio in the predetermined region. It is preferable that the region mammary gland ratio is a volume ratio of a mammary gland in the predetermined region.

It is preferable that the processor is configured to evaluate the extensibility using a rate of match calculated based on two region mammary gland ratios respectively calculated using the radiation image, and the region mammary gland ratio is a distribution of the pixel mammary gland ratios in the predetermined region.

It is preferable that the radiation image selected from the two radiation images is the radiation image obtained by imaging the left and right breasts of the subject, respectively.

It is preferable that the radiation image selected from the two radiation images is the radiation image obtained by imaging the breasts of the same subject at different points in time.

It is preferable that the processor is configured to: generate an operation instruction display based on the evaluation result of the extensibility and the region mammary gland ratio of the radiation image selected from a plurality of the radiation images; and perform control to display the operation instruction display.

It is preferable that the processor is configured to: classify breast compositions of each of the radiation images based on the pixel mammary gland ratio; and perform control to display the breast compositions.

According to another aspect of the present invention, there is provided an operation method of a radiation image processing apparatus, the operation method comprising: a step of acquiring two radiation images obtained by imaging breasts of the same subject; a step of calculating, based on the radiation images, a pixel mammary gland ratio, which is a ratio of a mammary gland for each pixel in each of the radiation images; a step of calculating, based on the pixel mammary gland ratio, a region mammary gland ratio in a predetermined region of each of the radiation images; a step of evaluating extensibility of the mammary gland by comparing two region mammary gland ratios respectively calculated using the two radiation images; and a step of performing control to display an evaluation result of the extensibility.

According to the aspects of the present invention, it is possible to improve the accuracy of evaluation of extensibility of the mammary gland.

Figure 3:
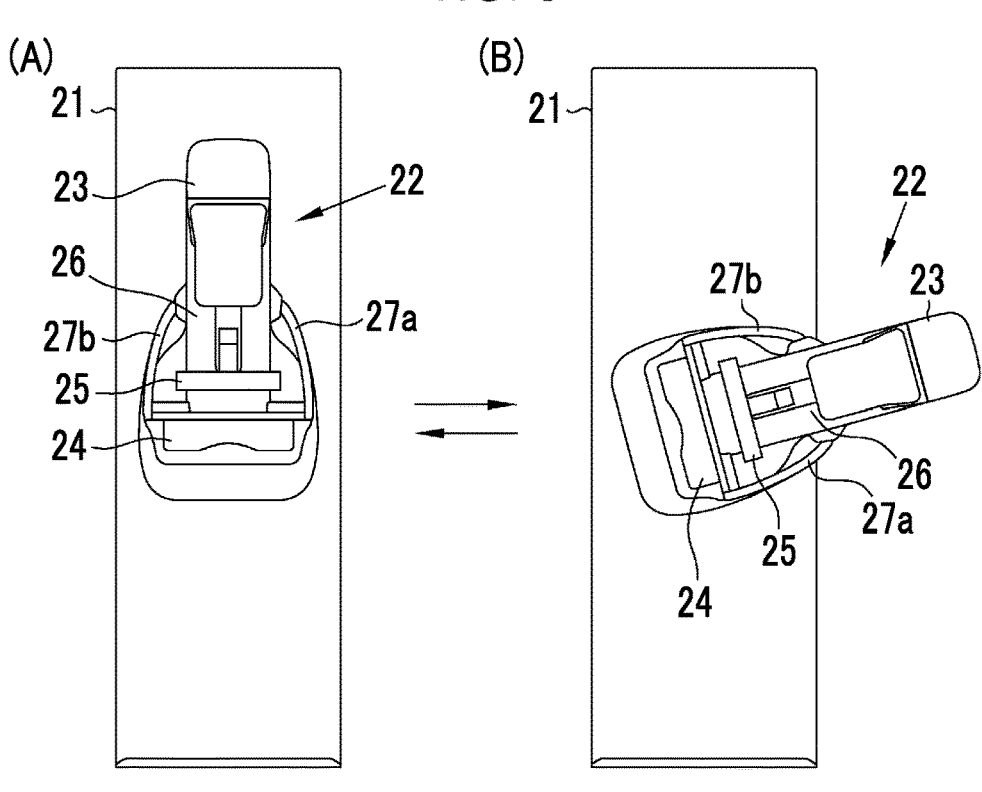

(A) and (B) of FIG. 3 are external views showing a mode in which a movable portion is rotated.

Figure 4:
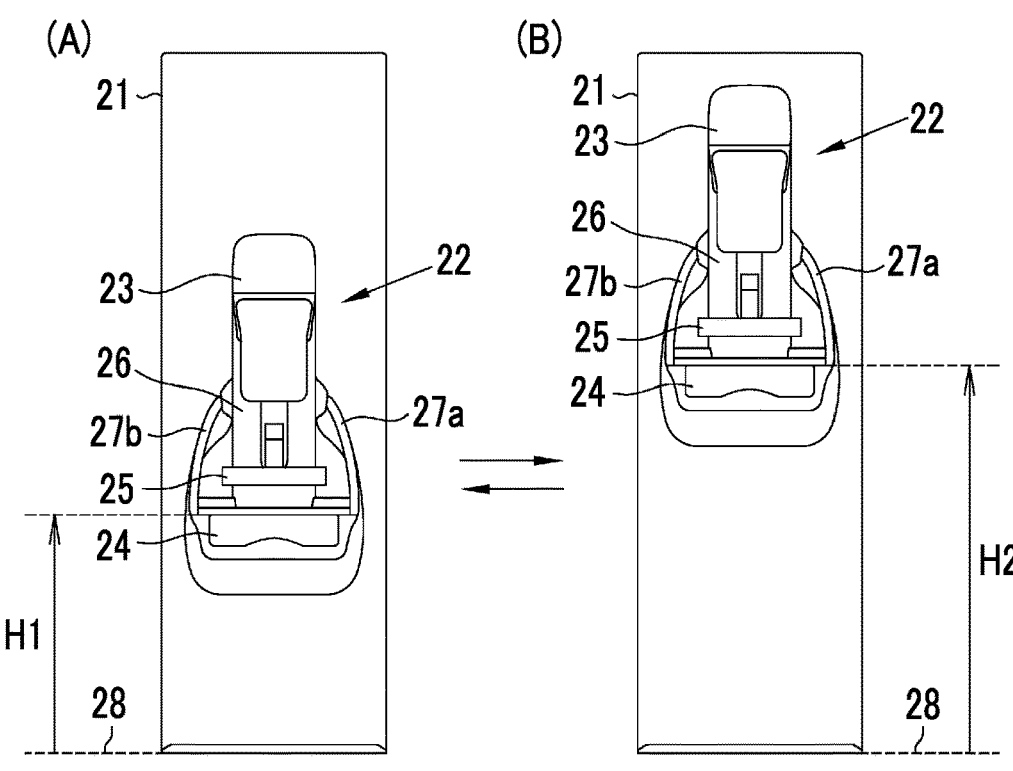

(A) and (B) of FIG. 4 are external views showing a mode in which the movable portion is moved in a vertical direction.

Figure 5:
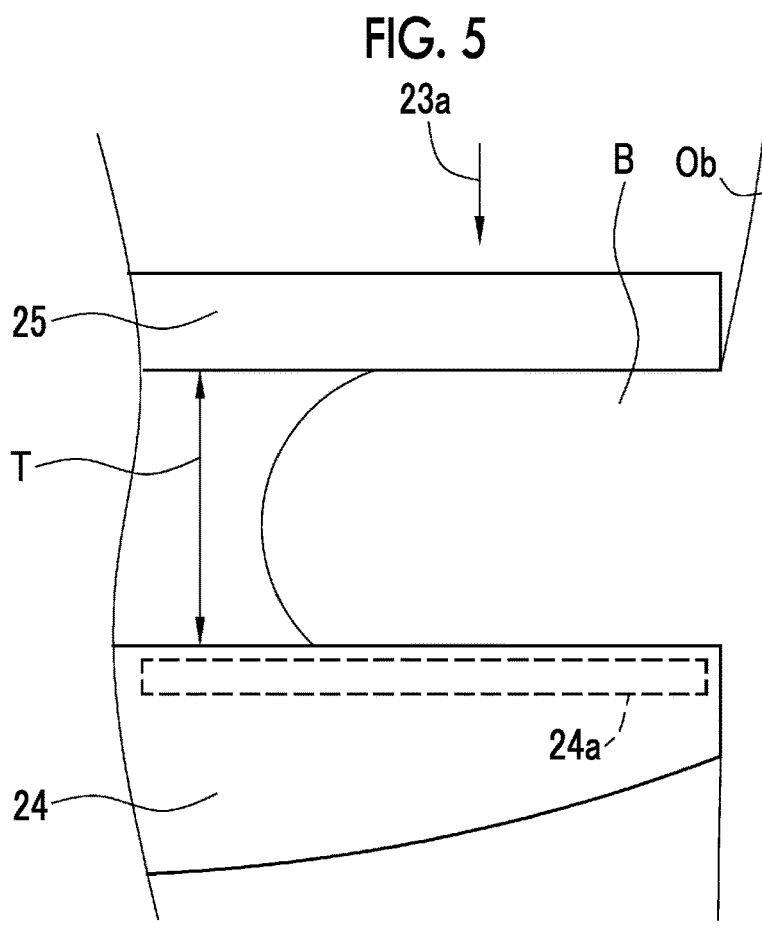

FIG. 5 is an explanatory diagram showing a method of capturing a radiation image using a mammography apparatus.

Figure 6:
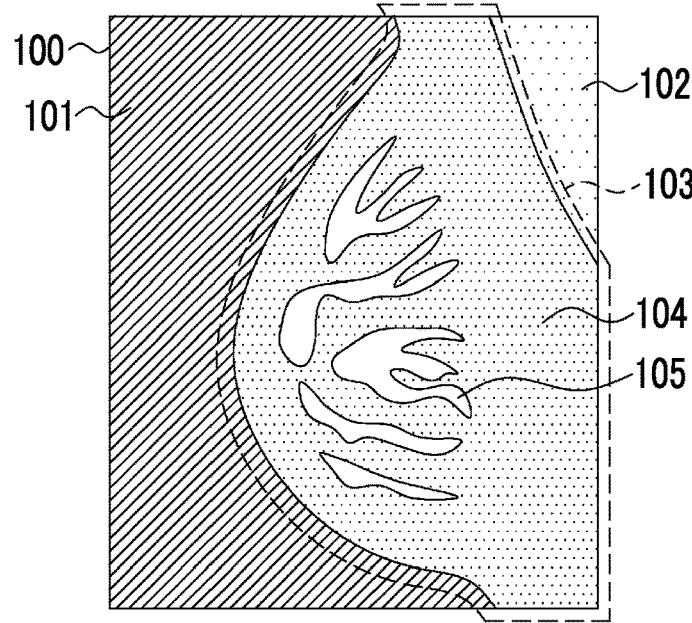

FIG. 6 is an image diagram showing an example of a region included in a radiation image.

Figure 7:
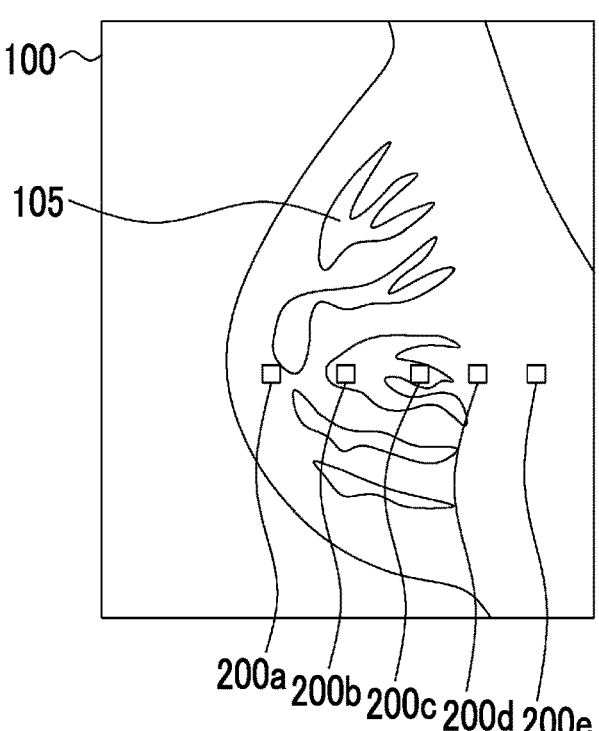

FIG. 7 is an image diagram showing an example of pixels included in a radiation image.

Figure 8:
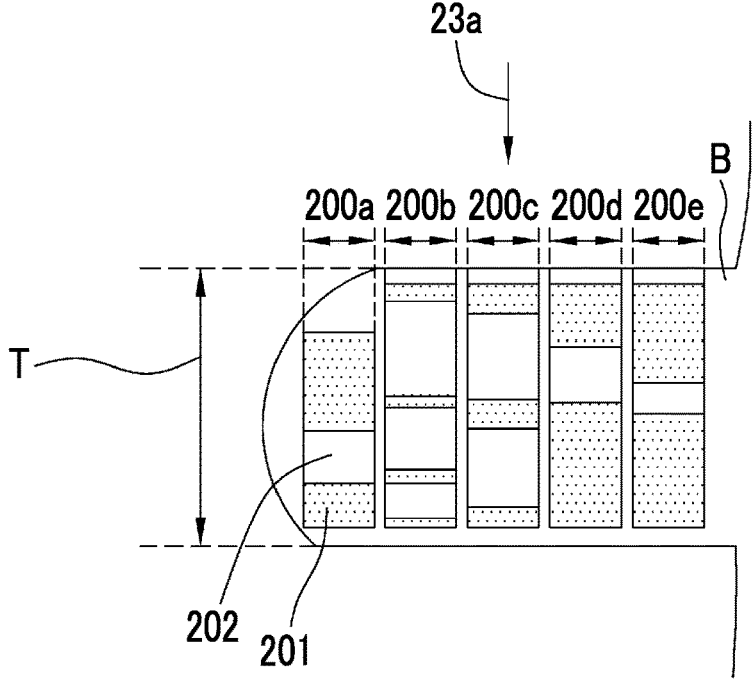

FIG. 8 is an explanatory diagram schematically showing adipose tissue and mammary gland tissue included in a breast corresponding to pixels of a radiation image.

Figure 9:
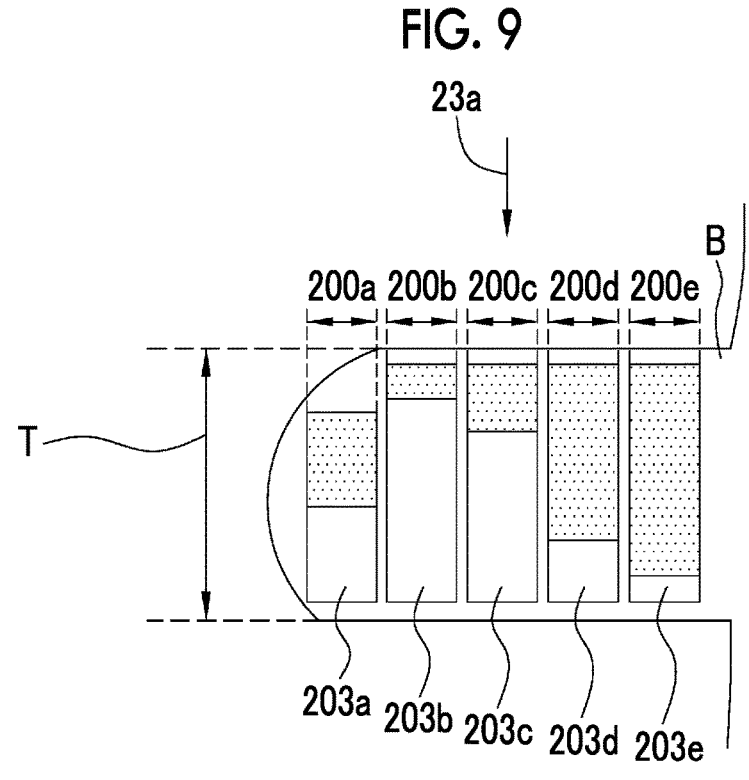

FIG. 9 is an explanatory diagram showing a pixel mammary gland ratio.

Figure 10:
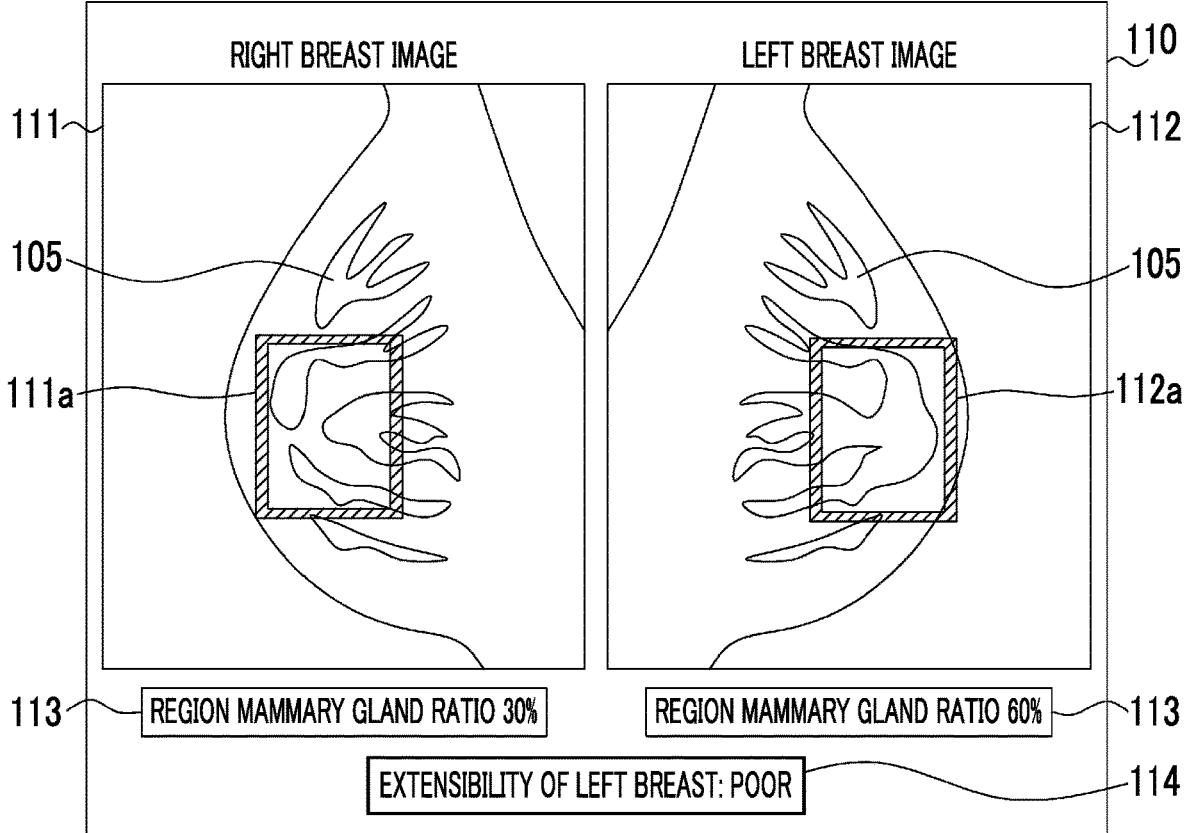

FIG. 10 is an image diagram showing an example of a display image in which an evaluation result as character information is displayed by comparing a right breast image and a left breast image.

Figure 11:
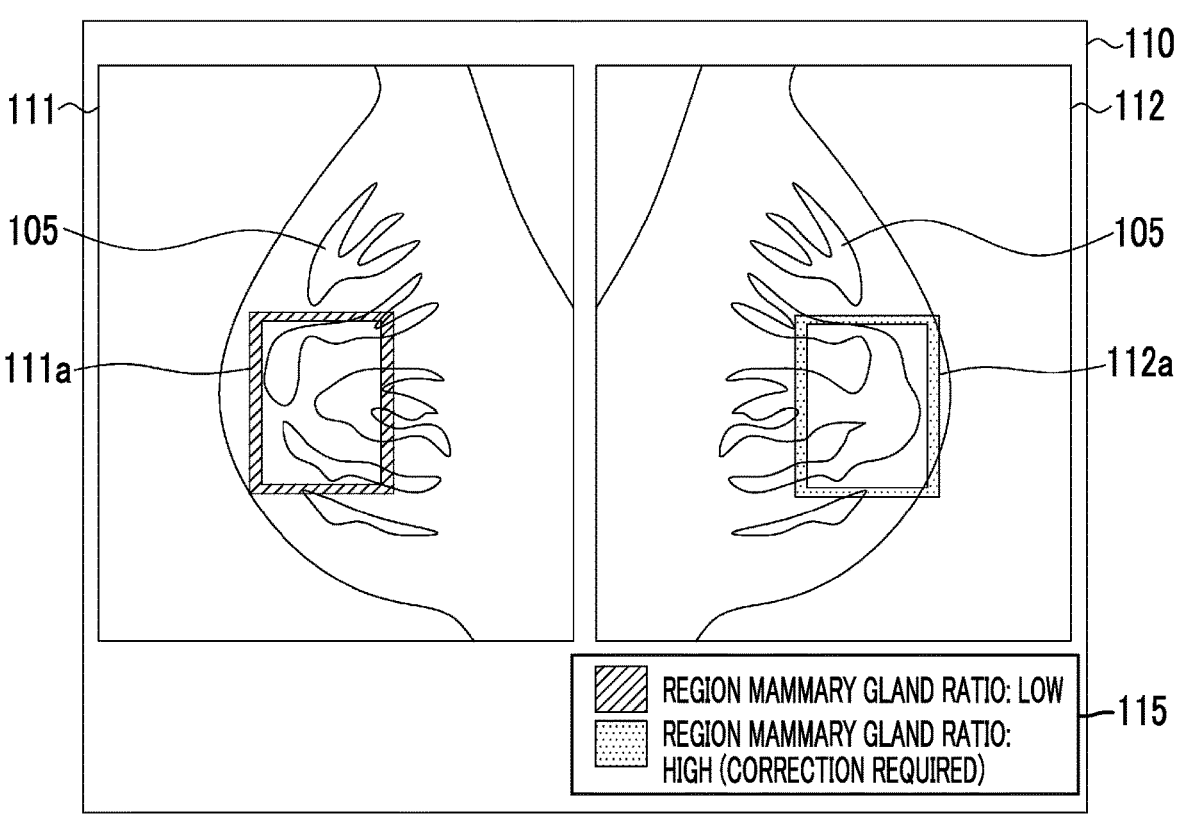

FIG. 11 is an image diagram showing an example of a display image in which an evaluation result is displayed by comparing a right breast image and a left breast image and differentiating markers indicating predetermined regions from each other.

Figure 12:
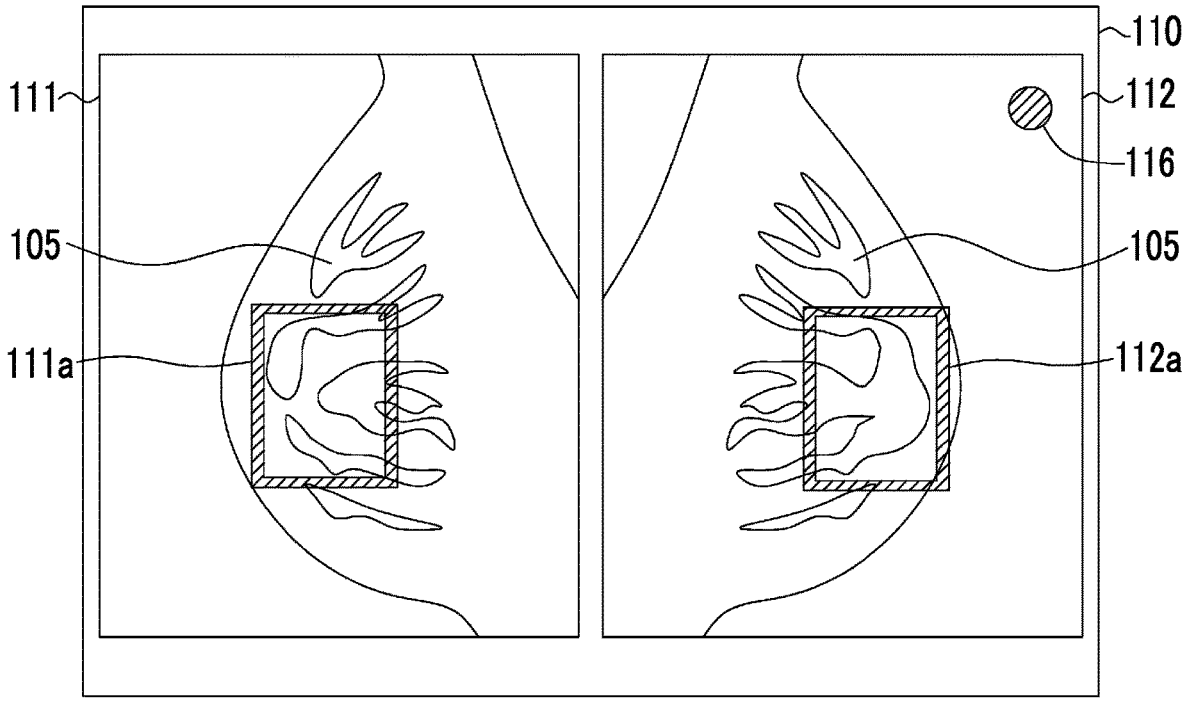

FIG. 12 is an image diagram showing an example of a display image in which an evaluation result is displayed by comparing a right breast image and a left breast image and displaying a warning marker.

Figure 13:
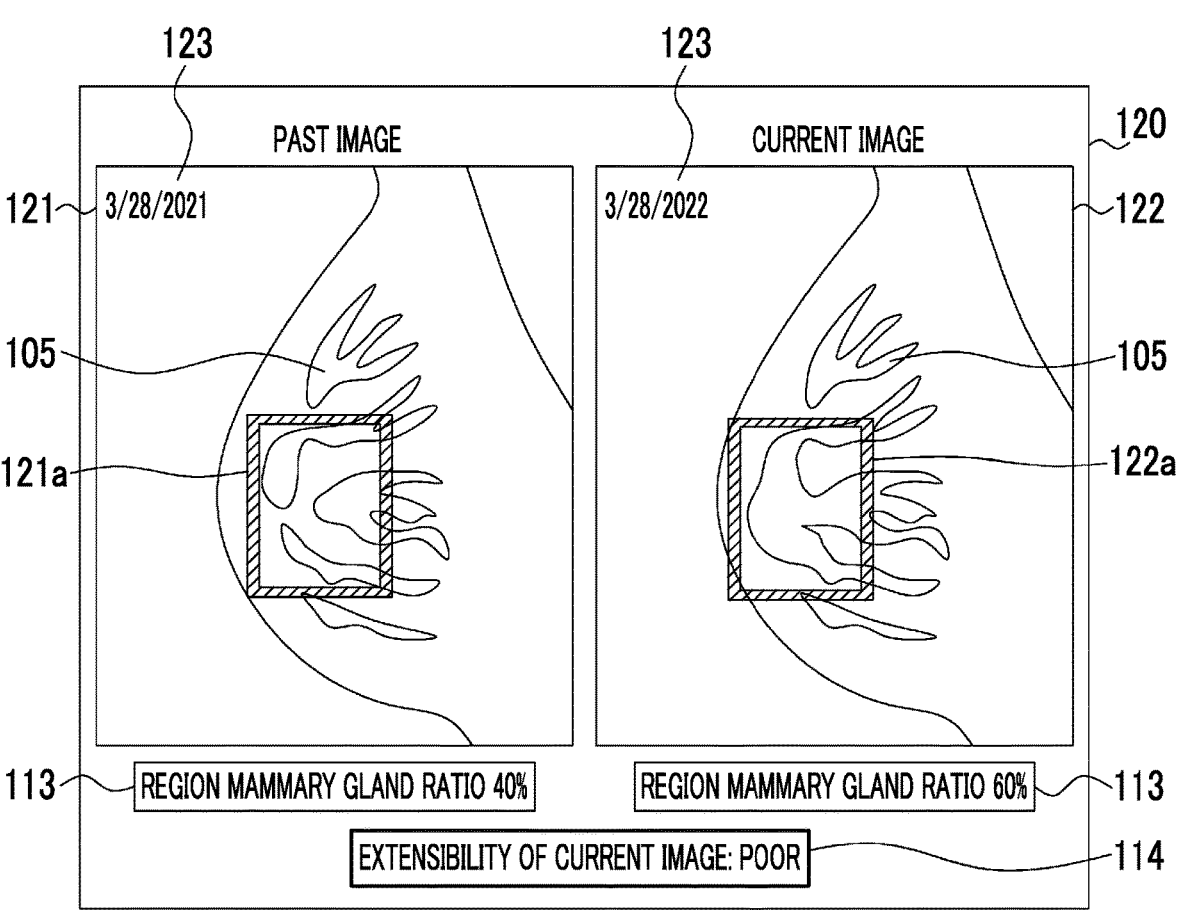

FIG. 13 is an image diagram showing an example of a display image in which an evaluation result as character information is displayed by comparing a past image and a current image.

Figure 14:
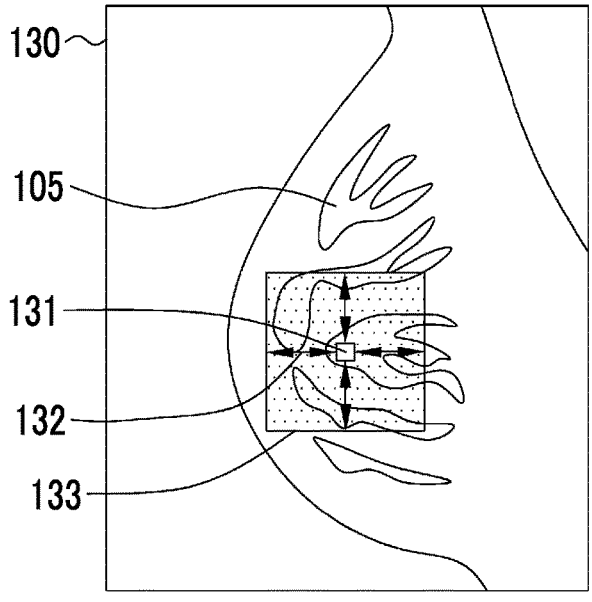

FIG. 14 is an image diagram showing an example in a case where a predetermined region is defined as a region within a specific distance range from a pixel having the maximum pixel mammary gland ratio.

Figure 15:
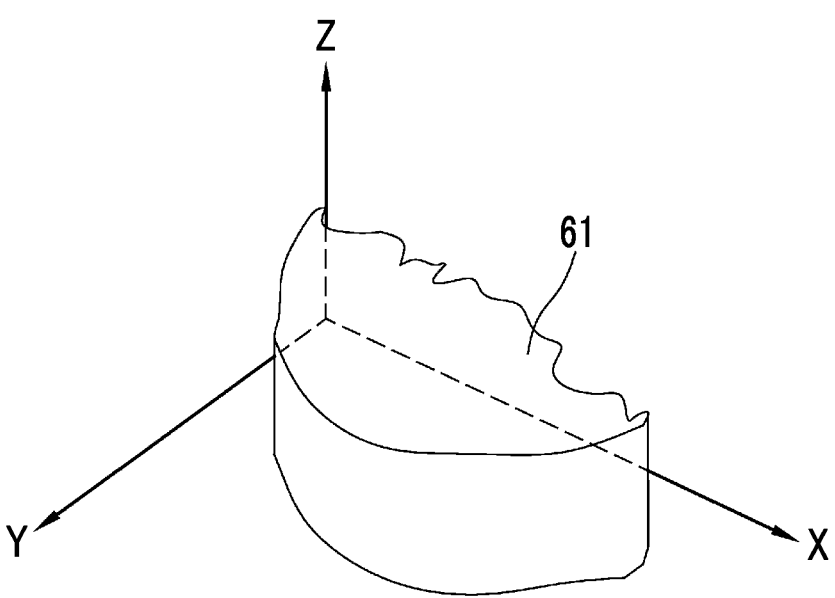

FIG. 15 is an explanatory diagram showing an example of a volume of a breast.

Figure 16:
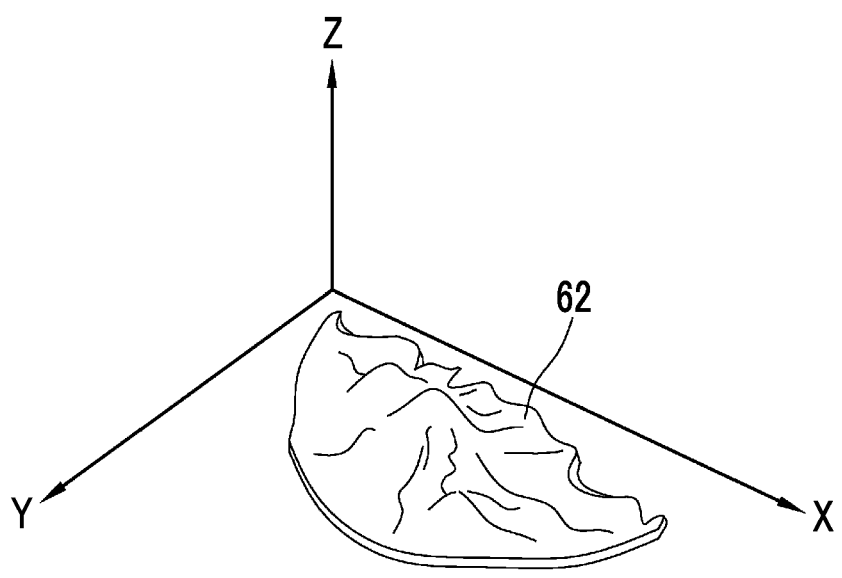

FIG. 16 is an explanatory diagram showing an example of a volume of a mammary gland.

Figure 17:
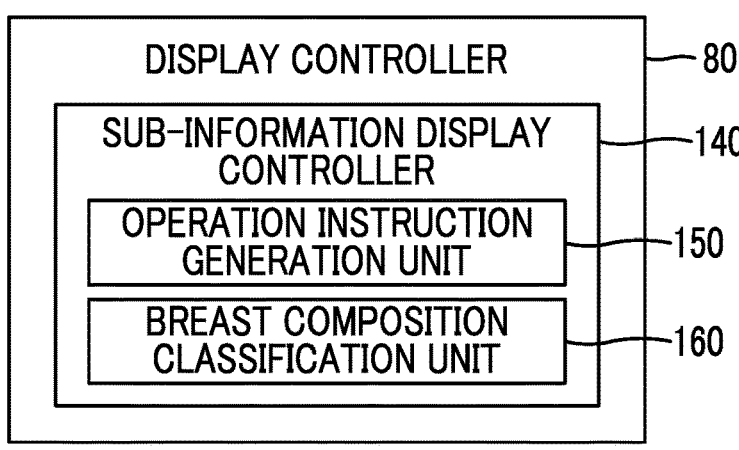

FIG. 17 is a block diagram showing functions of a display controller.

Figure 18:
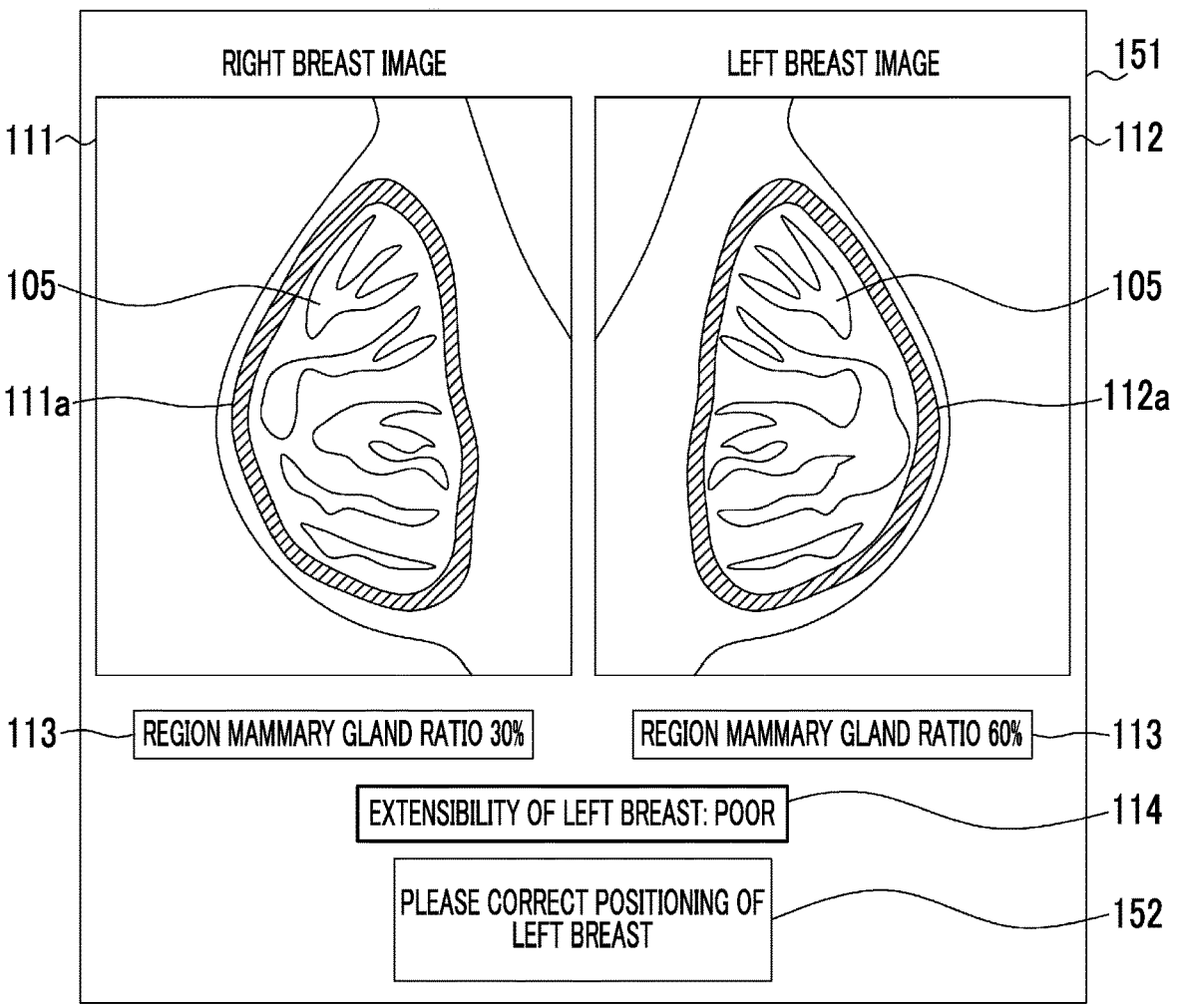

FIG. 18 is an image diagram showing an example of a display image in a case where an operation instruction display is displayed.

Figures 19, 20:
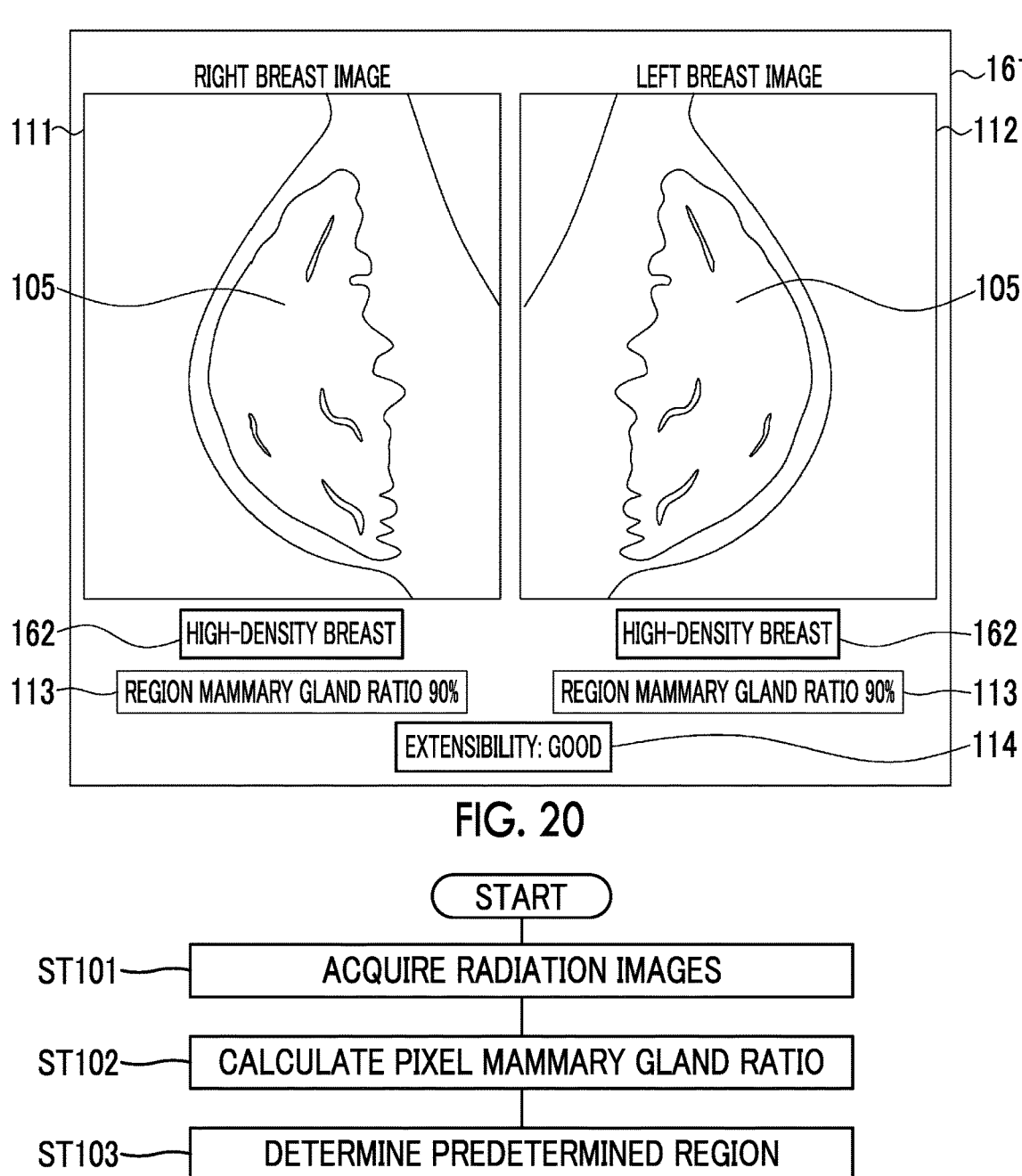

FIG. 19 is an image diagram showing an example of a display image in a case where a breast composition is displayed.

FIG. 20 is a flowchart showing an operation method of the radiation image processing apparatus.

DESCRIPTION OF THE PREFERRED EMBODIMENTS

Figure 1:
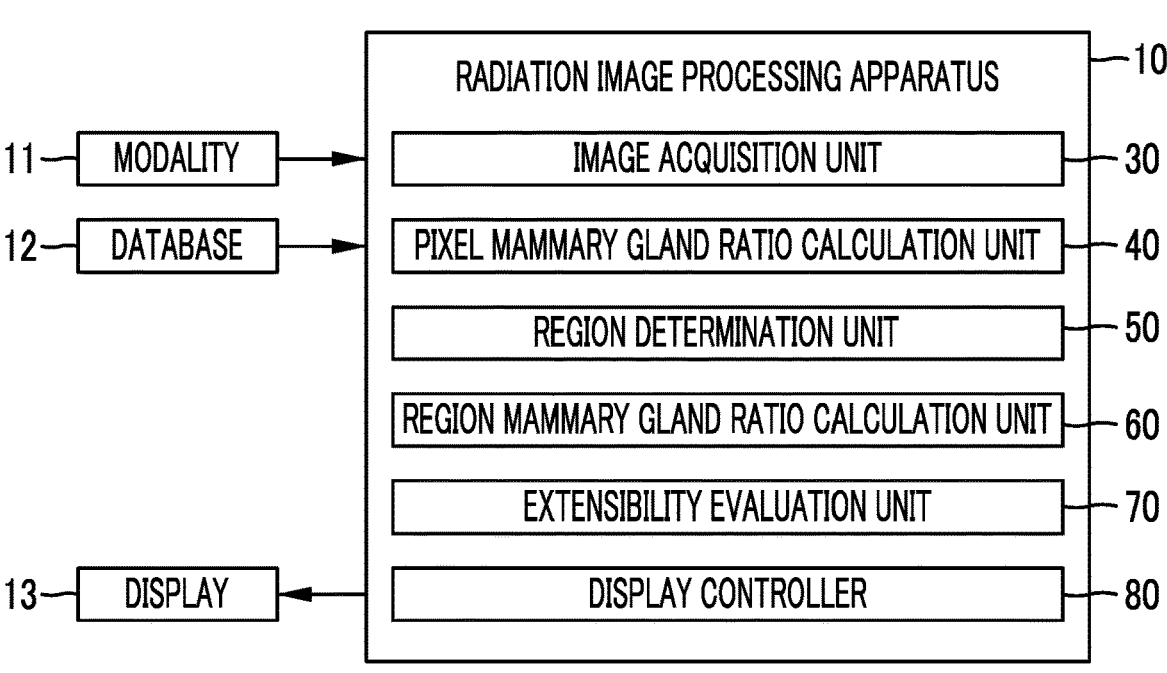
FIG. 1 is a block diagram showing a function of a radiation image processing apparatus.

As shown in FIG. 1, a radiation image processing apparatus 10 receives a radiation image from a modality 11 for capturing the radiation image or a database 12 in which the radiation image is saved. The radiation image is acquired by an image acquisition unit 30 of the radiation image processing apparatus 10. The radiation image processing apparatus 10, the modality 11, and the database 12 are connected to each other by wire or wirelessly via a network so as to be able to communicate with each other. The network is, for example, the Internet or a local area network (LAN).

As shown in FIG. 1, the radiation image processing apparatus 10 includes the image acquisition unit 30, a pixel mammary gland ratio calculation unit 40, a region determination unit 50, a region mammary gland ratio calculation unit 60, an extensibility evaluation unit 70, and a display controller 80. The radiation image processing apparatus 10 evaluates the extensibility by comparing a plurality of radiation images, and generates a display image for displaying an evaluation result of the extensibility. The display image is displayed on a display 13 so that a user such as a radiologist can visually recognize the image.

The radiation image processing apparatus 10 is a computer comprising a processor. Functions of the image acquisition unit 30, the pixel mammary gland ratio calculation unit 40, the region determination unit 50, the region mammary gland ratio calculation unit 60, the extensibility evaluation unit 70, and the display controller 80 are realized by a controller (not shown) configured by the processor operating programs related to various processes or controls incorporated in a program storage memory (not shown) provided in the radiation image processing apparatus 10.

Figure 2:
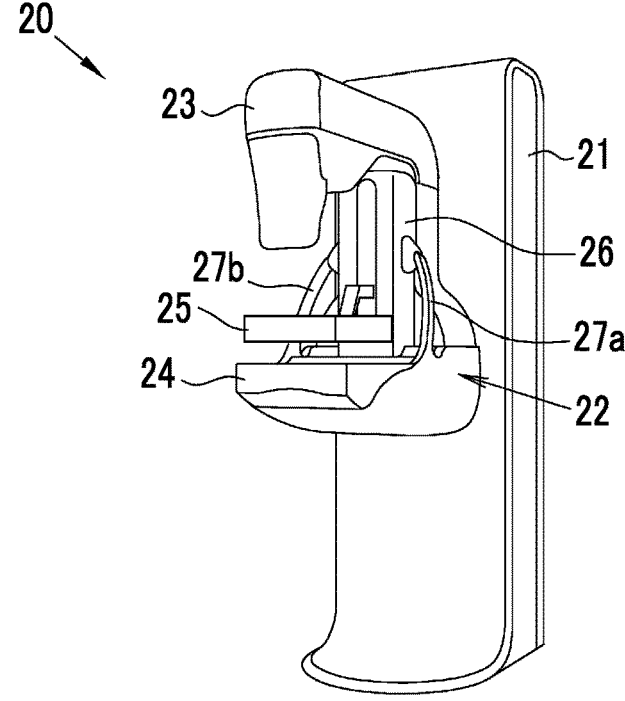
FIG. 2 is an external view of a mammography apparatus.

In the present embodiment, the modality 11 is a mammography apparatus 20. The mammography apparatus 20 is a radiation imaging apparatus that images a breast of a subject using radiation such as X-rays or gamma rays. As shown in FIG. 2, the mammography apparatus 20 comprises a support column 21 and a movable portion 22. The movable portion 22 comprises a radiation generation portion 23, an imaging table 24, a compression plate 25, and an elevating portion 26. In the movable portion 22, the radiation generation portion 23 and the imaging table 24 including a radiography unit incorporated therein are integrated, and further, in order to adjust the imaging position in a case where the subject is imaged using radiation, the movable portion 22 is freely movable in the vertical direction and is also rotatable within a predetermined angular range while maintaining the relative positions of the radiation generation portion 23 and the imaging table 24. The support column 21 supports the movable portion 22.

The radiation generation portion 23 emits radiation toward the radiography unit. In a case where the radiation generation portion 23 generates X-rays, the radiation generation portion 23 is an X-ray tube or a mono-tank in which the X-ray tube and other circuits are integrated. The radiography unit is a radiation detector that images a subject by using the radiation transmitted through the subject. The radiography unit is, for example, a flat panel detector (FPD).

The imaging table 24 is a stage on which the breast of the subject is placed, and the breast of the subject is sandwiched using the compression plate 25 at the time of imaging. Further, a grip portion 27a gripped by the subject with the right hand and a grip portion 27b gripped by the subject with the left hand are attached to the imaging table 24. The grip portion 27a and the grip portion 27b are so-called arm rests. The compression plate 25 compresses and flattens the breast of the subject placed on the imaging table 24. This is to reduce the overlap of normal mammary glands and to make it easier to find a lesion clearly in a case where there is a lesion. In a case of performing imaging, in order to obtain a radiation image suitable for interpretation, a user such as a radiologist performs positioning of the breast of the subject and then compresses the breast. The elevating portion 26 raises and lowers the compression plate 25 with respect to the imaging table 24. Thereby, the elevating portion 26 supports the compression plate 25 substantially parallel to the imaging table 24 and at a distance corresponding to the thickness of the breast.

As shown in (A) and (B) of FIG. 3, the movable portion 22 is rotatable within a predetermined angular range while maintaining the relative positions and orientations of the radiation generation portion 23 and the imaging table 24. Therefore, the mammography apparatus 20 can perform imaging by arranging the imaging table 24 horizontally or in an arrangement in which the imaging table 24 is inclined from the horizontal. Specifically, as shown in (A) of FIG. 3, in the mammography apparatus 20, the imaging table 24 is arranged horizontally, and cranio-caudal (CC) imaging in which the breast is imaged in the cranio-caudal direction can be performed. In addition, as shown in (B) of FIG. 3, in the mammography apparatus 20, the imaging table 24 is arranged to be inclined, and medio-lateral oblique (MLO) imaging in which the breast is imaged in the medial-lateral oblique direction can be performed. Although not shown, the mammography apparatus 20 can rotate the imaging table 24 and the like in a direction opposite to that in (B) of FIG. 3.

As shown in (A) and (B) of FIG. 4, the movable portion 22 is movable in a vertical direction while maintaining the relative positions and orientations of the radiation generation portion 23 and the imaging table 24. Therefore, the mammography apparatus 20 can adjust the height of the imaging table 24 according to the height of the subject and perform imaging in a comfortable posture. The height of the imaging table 24 is the height of the imaging table 24 with respect to a floor surface 28 (ground surface of the support column 21), and can be freely adjusted within a range of the minimum height H1 shown in (A) of FIG. 4 and the maximum height H2 shown in (B) of FIG. 4.

Radiation emitted from the radiation generation portion 23 transmits through the breast of the subject and is incident on the radiography unit, and a radiation image is captured by detecting the radiation. In mammography, usually, both a radiation image obtained by imaging a breast on the right side of a subject and a radiation image obtained by imaging a breast on the left side of the subject are acquired. The radiation images are transmitted to the radiation image processing apparatus 10 and/or the database 12.

The database 12 is a storage, a file server, a cloud storage, or the like for saving radiation images. The database 12 may be a part of a system such as radiology information systems (so-called RIS), hospital information systems (so-called HIS), or picture archiving and communication systems (PACS) that directly or indirectly cooperates with the radiation image processing apparatus 10. A plurality of radiation images saved in the database 12 are transmitted to the radiation image processing apparatus 10.

Hereinafter, a flow in which the radiation image processing apparatus 10 compares a plurality of radiation images obtained by imaging the breasts of the same subject and displays an evaluation result of extensibility will be described. The image acquisition unit 30 acquires two radiation images obtained by imaging the breasts of the same subject from the mammography apparatus 20 which is the modality 11 or the database 12. The two radiation images may be selected by a user such as a radiologist or a doctor, and the radiation image processing apparatus 10 may automatically select and acquire the two radiation images using the patient number attached to the radiation image, the imaging date and time, and the like. The image acquisition unit 30 transmits the received radiation images to the pixel mammary gland ratio calculation unit 40.

The "radiation image" in the present embodiment includes a pre-captured image (pre-shot image) in which the breast of the subject is imaged at a low dose for positioning adjustment during the examination. One of the two radiation images acquired by the image acquisition unit 30 may be used as a pre-shot image.

The pixel mammary gland ratio calculation unit 40 calculates the pixel mammary gland ratio for each pixel of each radiation image. The pixel mammary gland ratio is a mammary gland ratio for each pixel of the radiation image. The mammary gland ratio is a ratio of the mammary gland tissue in the region of the breast corresponding to each pixel constituting the radiation image in the thickness direction of the breast.

Hereinafter, the pixel mammary gland ratio will be described. First, a radiation image captured by the mammography apparatus 20 will be described. In mammography, as shown in FIG. 5, a breast B of a subject Ob placed on the imaging table 24 is compressed and extended by the compression plate 25, and then irradiated with radiation 23a. At this time, the distance between the compression plate 25 and the imaging table 24 is a thickness T of the breast. A radiography unit 24a incorporated in the imaging table 24 detects radiation transmitted through the breast B in the direction of the imaging table 24 from the compression plate 25, and obtains a radiation image 100 as shown in FIG. 6.

A specific example of the radiation image 100 shown in FIG. 6 is an example of a radiation image obtained by performing MLO imaging. The radiation image 100 includes a direct region 101, which is a transparent region in which the radiation does not transmit through the breast B of the subject Ob and is directly emitted to the radiography unit, and a pectoralis major region 102 that transmitted through the pectoralis major of the subject Ob. The region excluding the direct region 101 and the pectoralis major region 102 from the radiation image 100 is a breast region 103 (indicated by a broken line).

The breast B drawn on the radiation image as the breast region 103 is mainly composed of adipose tissue and mammary gland tissue. The adipose tissue is relatively difficult to absorb radiation and transmits radiation well. Therefore, the region of the radiation image 100 that contains a large amount of adipose tissue is displayed in black as a low absorption region 104. On the other hand, the mammary gland tissue absorbs radiation relatively well and is difficult to transmit radiation. Therefore, the region of the radiation image 100 that contains a large amount of mammary gland tissue is displayed in white as a high absorption region 105.

In FIG. 6, in the breast region 103, the low absorption region 104 in which a large amount of adipose tissue is contained and the high absorption region 105 in which a large amount of mammary gland tissue is contained are mixed in the plane direction. In addition, in FIG. 6, the direct region 101, the pectoralis major region 102, and the low absorption region 104 are shown with different patterns and the high absorption region 105 is unpatterned, which indicates that they are regions containing different absorbers or containing an absorber in different ratios. Further, in order to prevent the drawings from being complicated, the high absorption region 105 as a representative is designated by reference numerals in FIG. 6 and subsequent drawings showing examples of radiation images.

The pixel mammary gland ratio is calculated for each of pixels 200a, 200b, 200c, 200d, and 200e constituting the radiation image 100 as shown in FIG. 7. FIG. 7 shows the radiation image 100 obtained by irradiating the breast B with the radiation 23a from the front side to the back side of the paper surface (see FIG. 5). Further, in FIG. 7, the pixels 200a, 200b, 200c, 200d, and 200e are largely drawn for the sake of visibility of the drawing.

FIG. 8 schematically shows the adipose tissue 201 and the mammary gland tissue 202 included in the region of the breast B corresponding to each of the pixels 200*a*, 200*b*, 200*c*, 200*d*, and 200*e* of the radiation image 100 shown in FIG. 7. As shown in FIG. 8, in the region of the breast B corresponding to each of the pixels 200*a*, 200*b*, 200*c*, 200*d*, and 200*e*, the adipose tissue 201 (indicated by a dot pattern) and the mammary gland tissue 202 (indicated by an unpatterned region) are mixed in the direction of the thickness T of the breast. In addition, in FIG. 8 and FIG. 9 to be described later, the distance between the pixels is narrowly drawn for the sake of visibility of the drawing.

As shown in FIG. 9, considering attenuation by the adipose tissue 201 and attenuation by the mammary gland tissue 202 with respect to the radiation 23*a* emitted in the direction of the thickness T of the breast, the pixel mammary gland ratio calculation unit 40 calculates a pixel mammary gland ratio 203*a* to the pixel 200*a*, a pixel mammary gland ratio 203*b* to the pixel 200*b*, a pixel mammary gland ratio 203*c* to the pixel 200*c*, a pixel mammary gland ratio 203*d* to the pixel 200*d*, and a pixel mammary gland ratio 203*e* to the pixel 200*e*.

The pixel mammary gland ratio calculation unit 40 calculates how much the mammary gland tissue 202 is included in the adipose tissue 201 in the direction of the thickness T of the breast of the pixels constituting the radiation image as a pixel mammary gland ratio by using an attenuation coefficient of the adipose tissue 201 and an attenuation coefficient of the mammary gland tissue 202. Therefore, by calculating the pixel mammary gland ratio, it is possible to accurately represent how much mammary gland tissue exists in the region occupied by each pixel corresponding to each breast region, rather than a value that does not sufficiently consider the overlap of the mammary glands in the thickness direction of the breast, such as showing the density of the pixels of the radiation image with pixel values of 256 gradations, for example.

The pixel mammary gland ratio calculation unit 40 calculates, for example, the pixel mammary gland ratio 203*a* as 40%, the pixel mammary gland ratio 203*b* as 90%, the pixel mammary gland ratio 203*c* as 75%, the pixel mammary gland ratio 203*d* as 20%, and the pixel mammary gland ratio 203*e* as 10%, as numerical values between 0% and 100%.

Specifically, the pixel mammary gland ratio may be calculated by substituting the pixel value of the direct region 101, the pixel value of the adipose tissue pixel, and the pixel value of each pixel into the formula ([Equation 1]) for calculating the "mammary gland content" disclosed in JP2010-253245A. The adipose tissue pixel is a pixel corresponding to a portion of the breast that is estimated to be composed of only adipose tissue. The adipose tissue pixel may be a pixel having the largest transmission amount of the radiation 23*a* in the breast region 103, or may be a pixel having a pixel value equal to or greater than a threshold value for determining the adipose tissue pixel.

In addition, the pixel mammary gland ratio may be calculated by substituting the value obtained from the reach dose of the direct region 101, the value obtained from the reach dose of the adipose tissue pixel, the value obtained from the reach dose of the breast region 103 of each pixel, the attenuation coefficient of the adipose tissue, and the attenuation coefficient of the mammary gland tissue into the formula (Formula (1) or Formula (5)) for calculating the "ratio of a mammary gland" disclosed in JP2020-370A.

The region determination unit 50 determines a region for which the region mammary gland ratio is calculated using the pixel mammary gland ratio as a predetermined region.

The predetermined region is composed of a plurality of pixels and may be set by an input of a user or may be set automatically. The region determination unit 50 may set the breast region 103 as a predetermined region, or may have a pixel mammary gland ratio or a mammary gland concentration region having a pixel with a particularly large amount of mammary gland to be described later as a predetermined region, as which will be described later. Further, as will be described later, a local region, which is a region within a certain range from a certain pixel, may be set as a predetermined region.

The region mammary gland ratio calculation unit 60 calculates the region mammary gland ratio in a predetermined region by using the pixel mammary gland ratio calculated for each radiation image. As will be described later, the region mammary gland ratio may be a statistic of s pixel mammary gland ratio in a predetermined region, be a volume ratio of a mammary gland in a predetermined region, or be a distribution of pixel mammary gland ratios in a predetermined region. For example, the maximum value of the pixel mammary gland ratio in a predetermined region of a radiation image (right breast image) obtained by imaging the right breast of a subject is calculated as "30%" as the region mammary gland ratio. In addition, the maximum value of the pixel mammary gland ratio in a predetermined region of a radiation image (left breast image) obtained by imaging the left breast of the subject is calculated as "60%" as the region mammary gland ratio.

The region mammary gland ratio calculated for each radiation image by the region mammary gland ratio calculation unit 60 is transmitted to the extensibility evaluation unit 70. The extensibility evaluation unit 70 compares the region mammary gland ratios in each of the predetermined regions of the two radiation images, evaluates the extensibility, and outputs the evaluation result.

For example, in a case where the statistic of the pixel mammary gland ratio in the predetermined region is defined as the region mammary gland ratio, the extensibility evaluation unit 70 calculates a difference in the region mammary gland ratio in each predetermined region of the two radiation images, outputs an evaluation result of "good extensibility" in a case where the difference in the region mammary gland ratio is less than a threshold value for evaluating extensibility, and outputs "poor extensibility" of the predetermined region in the radiation image with a higher region mammary gland ratio in a case where the difference in the region mammary gland ratio is equal to or greater than a threshold value for evaluating extensibility.

In addition, in a case where the distribution of the pixel mammary gland ratios in a predetermined region is defined as the region mammary gland ratio, as will be described later, the extensibility evaluation unit 70 may set the distribution of the pixel mammary gland ratios in the predetermined region for each radiation image as the region mammary gland ratio by representing the distribution of the pixel mammary gland ratios with a histogram having the lateral axis representing the pixel mammary gland ratio and the vertical axis representing the frequency (the number of pixels with a pixel mammary gland ratio belonging to each pixel mammary gland ratio class), and output an evaluation result of "good extensibility" or "poor extensibility" based on the relationship between the rate of match obtained by comparing the two histograms and a threshold value for evaluating the rate of match.

The two radiation images compared by the extensibility evaluation unit 70 are preferably radiation images obtained by imaging the left and right breasts of the same subject, respectively, or radiation images obtained by imaging either the left breast or the right breast of the same subject at different points in time.

Hereinafter, an example will be described in which the extensibility evaluation unit 70 evaluates extensibility by comparing region mammary gland ratios calculated from radiation images obtained by imaging left and right breasts, respectively in a case where the maximum value of the pixel mammary gland ratio in a predetermined region is defined as the region mammary gland ratio.

In a case where the region mammary gland ratio calculation unit 60 calculates the maximum value of the pixel mammary gland ratio in a predetermined region of the right breast image as 30% and the maximum value of the pixel mammary gland ratio in a predetermined region of the left breast image as 60%, the extensibility evaluation unit 70 calculates the difference in the region mammary gland ratio between the right breast image and the left breast image as "30%". Here, in a case where the threshold value for evaluating extensibility is set to "10%" in advance, and the fact that "the radiation image with a higher region mammary gland ratio is evaluated as poor extensibility in a case where the difference in the region mammary gland ratio is equal to or greater than the threshold value for evaluating extensibility" is set, the extensibility evaluation unit 70 outputs the evaluation result of "extensibility of the left breast image is poor (poor extensibility). The output evaluation result of extensibility is transmitted to the display controller 80.

The threshold value for evaluating extensibility can be set to any value. In addition, in a case where the region mammary gland ratio calculation unit 60 calculates a plurality of types of region mammary gland ratios such as "the maximum value of the pixel mammary gland ratio in a predetermined region" and "the volume ratio of a mammary gland in a predetermined region" for each radiation image, the user may set in advance a plurality of different threshold values for evaluating extensibility for each type of region mammary gland ratio. In addition, the plurality of threshold values for evaluating extensibility may be automatically set based on a plurality of types of threshold values for evaluating extensibility or the like that have been used in the past by the extensibility evaluation unit 70.

The display controller 80 generates a display image for displaying the evaluation result of the extensibility, and controls the display 13 connected to the radiation image processing apparatus 10 to display a display image. A specific example of the display image will be described with reference to FIG. 10. In a specific example of a display image 110 shown in FIG. 10, the region mammary gland ratio within the range of a marker 111a indicating a predetermined region of a right breast image 111 is calculated as 30% and the region mammary gland ratio within the range of a marker 112a indicating a predetermined region of a left breast image 112 is calculated as 60%, which are displayed in region mammary gland ratio display fields 113, respectively. The example shown in FIG. 10 is an example in a case of "a radiation image with a higher region mammary gland ratio is evaluated as poor extensibility in a case where a threshold value for evaluating extensibility is 10% or more", and "extensibility of the left breast: poor" is displayed in an evaluation result display field 114.

Here, the evaluation result is output with respect to the extensibility of the "predetermined region in the radiation image" with a higher region mammary gland ratio, but as the display of the evaluation result, the evaluation result of the extensibility of the "breast shown in the radiation image" with a higher region mammary gland ratio may be used. In addition, it is preferable that the radiation image is attached with information indicating whether the image is captured from the left or right breast, and information indicating the point in time of imaging such as the imaging date and time, such as the past image and the current image, which will be described later.

The markers 111a and 112a indicating the predetermined regions may or may not be displayed on the display image 110. Further, the threshold value for evaluating extensibility may be displayed. By displaying the display image 110 as shown in FIG. 10, in a case where the left breast image as a pre-shot image is captured after the right breast image is captured, it is possible to evaluate whether or not the mammary gland included in the breast shown in the pre-shot image has appropriate extensibility, and furthermore, in a case where the extensibility of the mammary gland shown in the pre-shot image is poor, it is possible to prompt the user to correct the positioning. In addition, in a case where the extensibility of the pre-shot image is good, it is possible to prompt re-imaging of the radiation image that has already been captured.

In addition, the display controller 80 may display the extensibility evaluation result by a display mode of a marker indicating a predetermined region or a warning display. In a case where the evaluation result of "extensibility of the left breast image is poor" is output, for example, as illustrated in FIG. 11, a legend 115 may be displayed by differentiating the display mode such as the color or pattern of a marker 111a indicating a predetermined region in the right breast image 111 and a marker 112b indicating a predetermined region in the left breast image 112 from each other according to the amount of the region mammary gland ratio.

In addition, in a case where the evaluation result of "extensibility of the left breast image is poor" is output, as illustrated in FIG. 12, a display image may be generated in which markers 111a and 112a indicating predetermined regions are displayed, and furthermore, a warning marker 116 is displayed on the left breast image. As illustrated in FIG. 11 and FIG. 12, the visibility of the evaluation result can be improved by displaying the evaluation result of the extensibility without using character information. The method of displaying the extensibility evaluation result is not limited thereto. For example, in a case of "poor extensibility", a radiation image with a high region mammary gland ratio may be surrounded by a warning frame.

The radiation images obtained by imaging the left and right breasts of the same subject usually have symmetry and are very similar. Therefore, in mammography of the same subject having the same imaging conditions such as a tube current value, an irradiation time, and a compression force on the breast, in a case where the difference in mammary gland extensibility by comparing the right breast image and the left breast image is large to some extent, it is considered that poor positioning of the right or left breast has occurred. Therefore, by evaluating the extensibility using the right breast image and the left breast image, in a case where either the right breast image or the left breast image is a pre-shot image, it is possible to prompt the user to correct the positioning or perform re-imaging.

In addition, the size of the breast and the amount of the mammary gland included in the breast vary greatly among individuals. Therefore, even though it is possible to obtain a radiation image in which the mammary gland tissue of a certain subject is sufficiently extended, it is difficult to correctly evaluate the extensibility of mammary gland by comparing a radiation image obtained by imaging the breast of a subject with a radiation image obtained by imaging the breast of a different subject. With the above configuration, by comparing radiation images obtained by imaging the breasts of the same subject, it is possible to evaluate the extensibility of the mammary gland while reducing the influence of individual differences in the breasts between the subjects.

Next, an example will be described in which the extensibility evaluation unit 70 evaluates extensibility by comparing region mammary gland ratios calculated from radiation images obtained by imaging either the left or right breast of the subject at different points in time in a case where the maximum value of the pixel mammary gland ratio in a predetermined region is defined as the region mammary gland ratio.

For example, in a case where the region mammary gland ratio calculation unit 60 calculates the maximum value of the pixel mammary gland ratio in a predetermined region of a radiation image (past image) captured in the past as 40% as the region mammary gland ratio and the maximum value of the pixel mammary gland ratio in a predetermined region of a radiation image (current image) that is a pre-shot image captured in the current examination as 60% as the region mammary gland ratio, the extensibility evaluation unit 70 calculates the difference in region mammary gland ratio between the past image and the current image as 20%. Here, in a case where the threshold value for evaluating extensibility is set to "10%" in advance, and the fact that "extensibility is evaluated as poor in a case where the difference in the region mammary gland ratio is equal to or greater than the threshold value for evaluating extensibility" is set, the extensibility evaluation unit 70 outputs the evaluation result of "extensibility of the current image is poor (poor extensibility).

FIG. 13 shows an example of a display image 120 generated by the display controller 80 in a case where radiation images captured at different points in time are compared. The region mammary gland ratio within the range of a marker 121*a* indicating a predetermined region of a past image 121 attached with an imaging date 123 of "2021/3/28" when the right breast was imaged is calculated as 40% and the region mammary gland ratio within the range of a marker 122*a* indicating a predetermined region of a current image 122 attached with an imaging date 123 of "2022/3/28" when the right breast was imaged is calculated as 60%, which are displayed in region mammary gland ratio display fields 113, respectively. In addition, in an evaluation result display field 114, "extensibility of current image: poor" is displayed. In an example in which the extensibility evaluation unit 70 outputs an evaluation result of poor extensibility in a case where the threshold value for evaluating extensibility is 10% or more, such display is performed. Note that FIG. 13 shows an example in which a right breast image captured in the past and a right breast image captured in the current examination are compared with each other.

In a case of normal adult women who are not pregnant, the ratio of mammary glands generally rarely changes abruptly in 1 to 2 years. Therefore, in a case where the time difference between the past and current examinations is about 1 to 2 years, it can be said that the ratios of mammary glands calculated from the radiation images captured at the past point in time and the current point in time are similar. Therefore, in mammography of the same subject having the same imaging conditions such as a tube current value, an irradiation time, and a compression force on the breast, in a case where the difference in mammary gland extensibility by comparing the past image and the current image is large to some extent, it is considered that poor positioning of the breast in the past or current image has occurred. Therefore, it is possible to evaluate whether the positioning is good or poor by comparing the region mammary gland ratios between the past image and the current image. Further, in a case where the current image is a pre-shot image, it is possible to prompt the user to correct the positioning.

The radiation images compared by the extensibility evaluation unit 70 may be obtained by comparing radiation images of contralateral breasts captured at different points in time to evaluate extensibility such that the radiation image of the left breast captured in the past and the radiation image of the right breast captured in the current examination of the same subject are compared with each other. This is because these radiation images are similar.

With the above configuration, it is possible to accurately and easily determine whether or not an ideal radiation image has been captured by comparing the region mammary gland ratios in consideration of how much mammary gland tissue is included in the thickness direction of the breast sandwiched between the compression plate and the imaging table for each predetermined region. Further, in a case where the evaluation result of the extensibility comparing two radiation images in which one of them is a pre-shot image is poor, since the positioning of the radiation image with the higher region mammary gland ratio is inappropriate, displaying the evaluation result of the extensibility can prompt the user to correct the positioning. Further, it is possible to confirm and examine whether or not the positioning of not only the pre-shot image but also the radiation image captured in the past by the radiologist is appropriate.

An example of a method for determining a predetermined region in the present embodiment will be described below. As described above, the region determination unit 50 can set the breast region 103, the mammary gland concentration region, or the local region as a predetermined region.

In a first example in a case where the mammary gland concentration region is set as a predetermined region, the region determination unit 50 may set a region having pixels in which the pixel mammary gland ratio is equal to or greater than the first determination threshold value as the mammary gland concentration region. A breast region in the radiation image includes a low absorption region with a lot of adipose tissue, a high absorption region with a lot of mammary gland tissue, and a region (intermediate absorption region) that belongs to the middle between the low absorption region and the high absorption region. By setting the mammary gland concentration region according to the first determination threshold value, it is possible to calculate the region mammary gland ratio after excluding the low absorption region which does not significantly affect the evaluation of the extensibility of the mammary gland from the predetermined region. That is, by setting only the regions (high absorption region and intermediate absorption region) that particularly affect the evaluation of the extensibility of the mammary gland tissue as the calculation target of the region mammary gland ratio, it is possible to evaluate the extensibility of mammary glands by reducing the influence of the noise region, rather than comparing radiation images on a pixel-by-pixel basis or the radiation image as a whole. The first determination threshold value can be freely set.

In a second example in a case where the mammary gland concentration region is set as a predetermined region, the region determination unit 50 may set, as the mammary gland concentration region, a region having pixels in which the mammary gland amount is equal to or greater than the second determination threshold value in the radiation image. The mammary gland amount is an estimated value of the volume of the mammary gland tissue which is the product of the pixel mammary gland ratio and the thickness of the breast corresponding to the distance between the compression plate and the imaging table. With the above configuration, by calculating the mammary gland amount for each pixel using the pixel mammary gland ratio and determining a predetermined region based on the mammary gland amounts, from the viewpoint of the volume of mammary gland tissue, a region that is considered to greatly affect the evaluation of extensibility of the mammary gland can be used as a calculation target of the region mammary gland ratio. It is preferable to set the mammary gland concentration region as a predetermined region because the mammary gland concentration region is a region in which it is difficult to distinguish a normal mammary gland tissue from a lesion and attention should be paid to observation.

In a case where a local region is set as a predetermined region, the region determination unit 50 may set, as the predetermined region, a region within a specific distance range from the pixel in which the pixel mammary gland ratio is maximum in the radiation image. Specifically, as shown in FIG. 14, the region determination unit 50 determines, in a radiation image 130, a region within a range of a specific distance 132 (indicated by arrows) from a pixel 131 in which the pixel mammary gland ratio is maximum as a predetermined region 133 (indicated by a dot pattern). The specific distance can be freely set, for example, within a range of 10 pixels above and below the pixel 131 in which the pixel mammary gland ratio is maximum. In addition, a specific distance range, which is a predetermined region, is determined by using, for example, coordinate information of the pixel in which the pixel mammary gland ratio is maximum and a specific distance. By setting the specific distance to a small value, the region mammary gland ratio can be calculated by focusing on the region around the pixel in which the pixel mammary gland ratio is maximum, which is a local region in which the extensibility is likely to be poor, and used for the extensibility evaluation.

As described above, by setting the mammary gland concentration region or the local region as the predetermined region, the influence of the noise region can be reduced, and the extensibility of the mammary gland can be evaluated more accurately. In addition, it is possible to make a comparison only in partial regions of the two radiation images in which the mammary gland tissue is solidified. It is difficult even for an experienced radiologist to perform an extensibility evaluation by comparing small parts of a radiation image, which is a part where the mammary gland tissue is solidified and is considered to have a high likelihood that the extensibility is not good for the user. In particular, in a normal examination in which not only accuracy but also quickness is required, it is difficult to carefully observe small parts of a radiation image. With the above configuration, it is possible to easily evaluate the extensibility of the mammary gland for a local portion of the radiation image even in a situation where the positioning is considered to be good to some extent. As a result, the examination can be smoothly performed and the burden on the subject can be reduced.

Hereinafter, an example of a method of calculating the region mammary gland ratio and a method of outputting an evaluation result of extensibility in the present embodiment will be described. In a first example in which the extensibility is evaluated based on the difference in the region mammary gland ratio, a statistic of the pixel mammary gland ratio in a predetermined region such as a breast region, a mammary gland concentration region, or a local region is defined as a region mammary gland ratio. A statistic includes a maximum value (see the example shown in FIGS. 10 to 13), a most frequent value, or an average value, but is not limited thereto. In this case, the extensibility evaluation unit 70 outputs the evaluation result of the extensibility using the relationship between the difference in the region mammary gland ratio and the threshold value for evaluating extensibility. With the above configuration, it is possible to calculate the region mammary gland ratio so that the burden of the calculation processing of the processor is relatively light.

In a second example in which the extensibility is evaluated based on the difference in the region mammary gland ratio, in a case where the extensibility is evaluated based on the difference in the region mammary gland ratio, the volume ratio of the mammary gland in the predetermined region is defined as the region mammary gland ratio. In this case, the predetermined region is preferably a mammary gland concentration region. In this example, the region mammary gland ratio calculation unit 60 may calculate a volume (a) of the breast in the predetermined region and a volume (b) of the mammary gland in the predetermined region, calculate a volume ratio of the mammary gland as (b)/(a), and define the volume ratio as a region mammary gland ratio. For example, as shown in FIG. 15, a volume (a) of the breast 61 in a predetermined region is calculated as the product of a predetermined region (unit: pixel) represented on a plane formed in the x-axis and y-axis directions and a distance (unit: millimeter) between the imaging table 24 and the compression plate 25 corresponding to the thickness of the breast, which is represented in the z-axis direction. As shown in FIG. 16, a volume (b) of the mammary gland 62 is calculated by obtaining a volume of the mammary gland in a pixel using the product of a distance (unit: millimeter) between the imaging table 24 and the compression plate 25 and the pixel mammary gland ratio, which is represented in the z-axis direction, and further calculating the volume of the mammary gland for each of all pixels included in a predetermined region represented on a plane formed in the x-axis and y-axis directions. Assuming that the predetermined region is a mammary gland concentration region, the volume ratio (b)/(a) of the mammary gland is the volume ratio of the mammary gland in the mammary gland concentration region.

In this case, the extensibility evaluation unit 70 outputs the evaluation result of the extensibility using the relationship between the difference in the volume ratio of the mammary gland calculated for each radiation image and the threshold value for evaluating extensibility. With the above configuration, it is possible to compare the volume of the mammary gland in a three-dimensional predetermined region in consideration of the direction in which radiation is detected and the thickness direction of the breast. In addition, in a case where a predetermined region is a mammary gland concentration region, by obtaining the volume ratio of the mammary gland in the mammary gland concentration region, it is possible to perform the evaluation after excluding the noise region in the evaluation of the extensibility.

In a case where the extensibility is evaluated using the rate of match of the distributions of the pixel mammary gland ratios, the region mammary gland ratio calculation unit 60 generates a histogram of the distribution of the pixel mammary gland ratios in a predetermined region of each radiation image and uses it as the region mammary gland ratio. In this histogram, the lateral axis represents the pixel mammary gland ratio and the vertical axis represents the frequency (the number of pixels having the pixel mammary gland ratio belonging to each class). The class width on the lateral axis may be freely set.

In this case, the extensibility evaluation unit 70 calculates the rate of match of the histograms of the respective radiation images by using a known method of comparing the histograms, such as the intersection method or the use of the Euclidean distance. Next, the evaluation result is output based on the relationship between the rate of match and the threshold value for evaluating the rate of match.

In a case where the extensibility evaluation unit 70 calculates the rate of match using the intersection method, the total number of pixels included in a predetermined region of the radiation image is normalized so that the total sum of the frequencies becomes 1, and the rate of match is calculated by substituting it into the function used in the intersection method. In this case, the rate of match is calculated as an output value, and the closer to 1, the higher the rate of match. For example, the extensibility evaluation unit 70 sets a threshold value for evaluating the rate of match to 0.9, and outputs an evaluation result of "good extensibility" in a case where the rate of match is equal to or greater than the threshold value for evaluating the rate of match and outputs an evaluation result of "poor extensibility" in a case where the rate of match is less than the threshold value for evaluating the rate of match.

Further, in a case where the extensibility evaluation unit 70 calculates the rate of match by using the Euclidean distance, each histogram is expressed as the coordinates in the multidimensional space, and the distance between the coordinates is calculated as the rate of match. In this case, the closer the distance between the coordinates is to 0, the higher the rate of match. For example, the extensibility evaluation unit 70 sets a threshold value for evaluating the rate of match to 0.1, and outputs an evaluation result of "good extensibility" in a case where the rate of match is less than the threshold value for evaluating the rate of match and outputs an evaluation result of "poor extensibility" in a case where the rate of match is equal to or greater than the threshold value for evaluating the rate of match. With the above configuration, even in a case where the thickness of the breast cannot be calculated accurately, the rate of match can be calculated by using the pixel mammary gland ratio in the predetermined region of each radiation image.

In addition, the extensibility evaluation unit 70 may output a plurality of evaluation results, integrate the plurality of evaluation results, and then calculate a final evaluation result, by using an evaluation result in a case where an average value of the pixel mammary gland ratios in the predetermined region is defined as the region mammary gland ratio as a first evaluation result, an evaluation result in a case where a volume ratio of the mammary gland in the predetermined region is defined as the region mammary gland ratio as a second evaluation result, a distribution of the pixel mammary gland ratios in the predetermined region as the region mammary gland ratio, and an evaluation result in a case where the rate of match is calculated using the intersection method as a third evaluation result. By calculating a plurality of evaluation results, the accuracy of the extensibility evaluation can be improved.

In the present embodiment, as shown in FIG. 17, the display controller 80 may further comprise a sub-information display controller 140. The sub-information display controller 140 further comprises an operation instruction generation unit 150 and a breast composition classification unit 160. The sub-information display controller 140 may comprise either the operation instruction generation unit 150 or the breast composition classification unit 160.

The operation instruction generation unit 150 generates an operation instruction display according to an operation instruction condition by using the region mammary gland ratio and the evaluation result. For example, as shown in FIG. 18, in a case where the region mammary gland ratio of the right breast image 111 within a range of a marker 111a indicating a predetermined region which is a mammary gland concentration region is 30%, and the region mammary gland ratio of the left breast image 112 within a range of a marker 112a indicating a predetermined region which is a mammary gland concentration region is 60%, and the operation instruction condition is set to "in the case of poor extensibility, issue a correction instruction for imaging conditions of radiation images with a high region mammary gland ratio", the operation instruction generation unit 150 generates an operation instruction display 152 of "Please correct the positioning of the left breast", transmits it to the display controller 80, and displays it on a display image 151. Further, the operation instruction generation unit 150 may generate an operation instruction display 152 that instructs the compression force of the compression plate 25 as a correction instruction of the imaging condition, such as "left breast compression force: A Newton". With the above configuration, it is possible to prompt the user to perform an operation such as positioning or compression force to perform re-imaging.

The breast composition classification unit 160 classifies the breast structure of the breast shown in the radiation image using the pixel mammary gland ratio. The breast composition classification unit 160 calculates a region mammary gland ratio for breast composition classification in the breast region using the pixel mammary gland ratio, and classifies the breast structure according to a relationship between the region mammary gland ratio for breast composition classification and a threshold value for breast composition classification. For example, using the pixel mammary gland ratio of the right breast image 111, the region mammary gland ratio for breast composition classification is calculated as "70%". In addition, using the pixel mammary gland ratio of the left breast image 112, the region mammary gland ratio for breast composition classification is calculated as "70%". The region on the radiation image for which the region mammary gland ratio for breast composition classification is to be calculated may be a breast region, a region preset by the user, or a region determined by setting a determination threshold value for determining regions for breast composition classification. The breast composition classification unit 160 determines the region on the radiation image for which the region mammary gland ratio for breast composition classification is to be calculated.

Examples of the setting of the threshold value for breast composition classification include "fatty" in a case where the region mammary gland ratio for breast composition classification is less than 10%, "scattered mammary gland" in a case where it is 10% or more and less than 50%, "heterogeneous high density" in a case where it is 50% or more and less than 80%, and "extremely high density in a case where it is 80% or more. In addition, "high-density breast" in a case where the region mammary gland ratio for breast composition classification is 50% or more and "non-high-density breast" in a case where it is less than 50% may be set. The method of setting the threshold value for breast composition classification is not limited thereto.

In a case where it is set in advance that classification is performed as "high-density breast" in a case where the threshold value for breast composition classification is 50% or more, and the breast composition classification unit 160 calculates the region mammary gland ratio for breast composition classification of the right breast image 111 as 70% and the region mammary gland ratio for breast composition classification of the left breast image 112 as 70%, the right breast image 111 and the left breast image 112 are classified as "high-density breast".

In the present embodiment, the breast structures classified by the relationship between the region mammary gland ratio for breast composition classification and the threshold value for breast composition classification are classified into "fatty", "scattered mammary gland", "heterogeneous high density", and "extremely high density" according to the amount of mammary gland tissue. In "fatty", it is easy to detect lesions because most of the mammary gland tissue is replaced with fat. In "scattered mammary gland", it is easy to detect lesions because it is a breast in which only mammary glands are observed in a cord-like manner due to replacement of mammary gland tissue with adipose tissue. In "heterogeneous high density", it is difficult to detect lesions because it is a breast in which fat is mixed in the parenchyma of the mammary gland. In "extremely high density", it is difficult to detect lesions because a breast in which fat is hardly mixed in the parenchyma of the mammary gland. Of these, breasts having "heterogeneous high density" and "extremely high density" are called high-density breasts (dense breasts) and require attention in discriminating lesions.

The breast composition classification unit 160 transmits information on the result of classifying the breast composition of each radiation image to the display controller 80. As shown in FIG. 19, the display controller 80 may display the result of classifying the breast compositions of the right breast image 111 and the left breast image 112 as a breast composition display field 162. In the example shown in FIG. 19, the right breast image 111 and the left breast image 112 are displayed as "high-density breast". In addition, the evaluation result of the extensibility is displayed as "extensibility: good".

As in the example shown in FIG. 19, in a case where the radiation images compared are high-density breasts, the region mammary gland ratio calculated from each radiation image is high, so that the evaluation of extensibility may not be accurate. Therefore, by displaying the breast composition with the above-described configuration, it is possible to prompt the user to pay attention to whether or not the extensibility is accurately evaluated.

In addition, for example, re-imaging a breast that is a high-density breast with a further increase in compression pressure may cause the subject to suffer more than necessary. In addition, it is possible to prompt the user to perform an examination using a modality (ultrasound imaging apparatus) other than mammography.

Furthermore, in such a radiation image of a high-density breast, since a large amount of mammary gland tissue is contained in the breast region, it is difficult to observe lesions such as calcification or a tumor that are displayed in white as a high absorption region as in the mammary gland tissue. Therefore, in addition to the high likelihood that the extensibility evaluation has not been performed accurately, the user is notified that there is a high likelihood that it is not possible to accurately discriminate whether or not the radiation image includes a lesion. Therefore, the breast composition display field 162 may be displayed only in a case where the imaged breast is a high-density breast.

A flow until the radiation image processing apparatus 10 displays the evaluation result of the extensibility using a plurality of radiation images of the same subject will be described with reference to the flowchart of FIG. 20. First, the image acquisition unit 30 acquires two radiation images from the modality 11 or the database 12 (Step ST101). Next, the pixel mammary gland ratio calculation unit 40 calculates the pixel mammary gland ratio for each pixel of each radiation image (Step ST102). Next, the region determination unit 50 reads out preset conditions to determine a predetermined region (Step ST103), and the region mammary gland ratio calculation unit 60 calculates the region mammary gland ratio in the predetermined region using the pixel mammary gland ratio (Step ST104). Next, the extensibility evaluation unit 70 compares the region mammary gland ratios of two radiation images of the same subject and outputs the evaluation result (Step ST105). Finally, the display controller 80 generates a display image for displaying the evaluation result (Step ST106). The generated display image is displayed on the display 13.

In the above embodiment, hardware structures of processing units for executing various processes, such as the image acquisition unit 30, the pixel mammary gland ratio calculation unit 40, the region determination unit 50, the region mammary gland ratio calculation unit 60, the extensibility evaluation unit 70, the display controller 80, the sub-information display controller 140, the operation instruction generation unit 150, and the breast composition classification unit 160, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a circuit configuration designed exclusively for executing various types of processing, and the like.

One processing unit may be configured by one of various processors, or may be configured by a combination of two or more processors of the same or different kinds (for example, a combination of a plurality of FPGAs or a combination of a CPU and an FPGA). In addition, a plurality of processing units may be configured by one processor. As an example of configuring a plurality of processing units via one processor, first, as represented by a computer, such as a client or a server, there is a form in which one processor is configured by a combination of one or more CPUs and software, and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as hardware structures.

More specifically, the hardware structure of these various processors is an electrical circuit (circuitry) in the form of a combination of circuit elements, such as semiconductor elements. The hardware structure of the storage unit is a storage device such as a hard disc drive (HDD) or a solid state drive (SSD).

EXPLANATION OF REFERENCES

10: radiation image processing apparatus
11: modality
12: database
13: display
20: mammography apparatus
21: support column
22: movable portion 23: radiation generation portion
23a: radiation
24: imaging table
24a: radiography unit
25: compression plate
26: elevating portion
27a, 27b: grip portion
28: floor surface
30: image acquisition unit
40: pixel mammary gland ratio calculation unit
50: region determination unit
60: region mammary gland ratio calculation unit
61: volume of breast
62: volume of mammary gland
70: extensibility evaluation unit
80: display controller
100, 130: radiation image
101: direct region
102: pectoralis major region
103: breast region
104: low absorption region
105: high absorption region
110, 120, 151, 161: display image
111: right breast image
111a, 112a, 112b, 121a, 122a: marker
112: left breast image
113: region mammary gland ratio display fields
114: evaluation result display field
115: legend
116: warning marker
121: past image
122: current image
123: imaging date
131, 200a, 200b, 200c, 200d, 200e: pixel
132: specific distance
133: predetermined region
140: sub-information display controller
150: operation instruction generation unit
152: operation instruction display
160: breast composition classification unit
162: breast composition display field
201: adipose tissue
202: mammary gland tissue
203a, 203b, 203c, 203d, 203e: pixel mammary gland ratio
B: breast
Ob: subject
T: thickness of breast

What is claimed is:
1. A radiation image processing apparatus comprising:
a processor configured to:
    acquire two radiation images obtained by imaging breasts of the same subject;
    calculate, based on the radiation images, a pixel mammary gland ratio, which is a ratio of a mammary gland for each pixel in each of the radiation images;
    calculate, based on the pixel mammary gland ratio, a region mammary gland ratio in a predetermined region of each of the radiation images;
    compare two region mammary gland ratios respectively calculated using the two radiation images; and
    perform control to display information indicating poor breast extensibility for a radiation image with the higher region mammary gland ratio of the two radiation images.
2. The radiation image processing apparatus according to claim 1, wherein the processor is configured to set, as the predetermined region, a region having the pixel in which the pixel mammary gland ratio is equal to or greater than a first determination threshold value in each of the radiation images.
3. The radiation image processing apparatus according to claim 1,
    wherein the processor is configured to:
        calculate a mammary gland amount for each pixel using the pixel mammary gland ratio; and
        set, as the predetermined region, a region having the pixel in which the mammary gland amount is equal to or greater than a second determination threshold value in each of the radiation images.
4. The radiation image processing apparatus according to claim 1,
    wherein the processor is configured to set, as the predetermined region, a region within a specific distance range from the pixel in which the pixel mammary gland ratio is maximum in each of the radiation images.
5. The radiation image processing apparatus according to claim 1,
    wherein the processor is configured to evaluate the extensibility based on a difference between two region mammary gland ratios respectively calculated using the two radiation images.
6. The radiation image processing apparatus according to claim 5,
    wherein the region mammary gland ratio is a statistic of the pixel mammary gland ratio in the predetermined region.
7. The radiation image processing apparatus according to claim 5,
    wherein the region mammary gland ratio is a volume ratio of a mammary gland in the predetermined region.
8. The radiation image processing apparatus according to claim 1,
    wherein the processor is configured to evaluate the extensibility using a rate of match calculated based on two region mammary gland ratios respectively calculated using the two radiation images, and
    the region mammary gland ratio is a distribution of the pixel mammary gland ratios in the predetermined region.
9. The radiation image processing apparatus according to claim 1,
    wherein the two radiation images are the radiation images obtained by imaging the left and right breasts of the subject, respectively.
10. The radiation image processing apparatus according to claim 1,
    wherein the two radiation images are the radiation images obtained by imaging the breasts of the same subject at different points in time.
11. The radiation image processing apparatus according to claim 1,
    wherein the processor is configured to:
        acquire a plurality of the radiation images obtained by imaging breasts of the same subject;
        calculate, based on the pixel mammary gland ratio, a region mammary gland ratio in a predetermined region of each of the plurality of radiation images;
        generate an operation instruction display based on the extensibility and the region mammary gland ratio of a radiation image selected from the plurality of the radiation images; and perform control to display the operation instruction display.

12. The radiation image processing apparatus according to claim 1, wherein the processor is configured to:

classify breast compositions of each of the radiation images based on the pixel mammary gland ratio; and perform control to display the breast compositions.

13. An operation method of a radiation image processing apparatus, the operation method comprising:

a step of acquiring two radiation images obtained by imaging breasts of the same subject;

a step of calculating, based on the radiation images, a pixel mammary gland ratio, which is a ratio of a mammary gland for each pixel in each of the radiation images;

a step of calculating, based on the pixel mammary gland ratio, a region mammary gland ratio in a predetermined region of each of the radiation images;

a step of comparing two region mammary gland ratios respectively calculated using the two radiation images; and a step of performing control to display information indicating poor breast extensibility for a radiation image with the higher region mammary gland ratio of the two radiation images.

\*    \*    \*    \*    \*